United States Patent [19]

Higashino et al.

[11] Patent Number: 5,200,415

[45] Date of Patent: Apr. 6, 1993

[54] PYRAZOLO[1,5-A]PYRIDINE-3-CARBOXYLIC ACID DERIVATIVES AND THEIR PHARMACEUTICAL USE

[75] Inventors: Takeo Higashino; Yukio Suzuki, both of Shizuoka; Takehiko Sasahara, Numazu; Tetsu Saito, Mishima; Daisuke Mochizuki, Shizuoka, all of Japan

[73] Assignee: Asahi Kasei Kogyo Kabushiki Kaisha, Osaka, Japan

[21] Appl. No.: 783,869

[22] Filed: Oct. 29, 1991

[30] Foreign Application Priority Data

Nov. 1, 1990 [JP] Japan .................. 2-297818
Nov. 27, 1990 [JP] Japan .................. 2-323807

[51] Int. Cl.$^5$ .................. A61K 31/44; C07D 471/02
[52] U.S. Cl. .................. 514/300; 546/121
[58] Field of Search .................. 546/121; 514/300

[56] References Cited

U.S. PATENT DOCUMENTS 4,822,795  4/1989  King .................. 514/214
5,034,398  7/1991  King .................. 546/112

OTHER PUBLICATIONS

Bermudez et al., J. Med. Chem., vol. 33, pp. 1924–1929.

*Primary Examiner*—Bernard Dentz
*Attorney, Agent, or Firm*—Young & Thompson

[57] ABSTRACT

Described herein are pyrazolo[1,5-a]pyridine-3-carboxylic acid derivatives represented by the following formula (I):

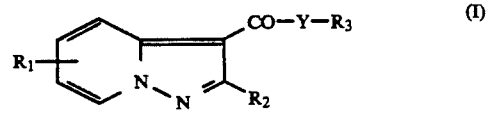

wherein $R_1$ and $R_2$ individually mean a hydrogen atom or a lower alkyl group, $R_3$ denotes an azabicyclo group containing a tertiary nitrogen atom, and Y stands for —O— or —NH—, or salts thereof. Their preparation process and serotonin receptor antagonists containing them as active ingredients are also described.

8 Claims, No Drawings

PYRAZOLO[1,5-A]PYRIDINE-3-CARBOXYLIC ACID DERIVATIVES AND THEIR PHARMACEUTICAL USE

BACKGROUND OF THE INVENTION

1) Field of the Invention

This invention relates to novel pyrazolo[1,5-a]-pyridine-3-carboxylic acid derivatives, and more specifically to pyrazolo[1,5-a]pyridine-3-carboxylic acid derivatives useful as drugs such as antiemetics and antianxietics and also to their preparation process and use.

2) Description of the Related Art

Compounds having serotonin receptor antagonism are known to be useful as neurotropics, antiemetics and the like, and many reports have been published on these compounds [EP 158,265 (corresponding to Japanese Patent Application Laid-Open No. 231677/1985), U.S. Pat. No. 4,886,808 (corresponding to Japanese Patent Application Laid-Open No. 275276/1986), U.S. Pat. No. 4,882,327 (corresponding to Japanese Patent Application Laid-Open No. 280061/1988), etc.]

SUMMARY OF THE INVENTION

It has however been desired to widely retrieve, find out and provide still better compounds having the pharmacological effects described above.

The present inventors have synthesized a variety of compounds and have studied their pharmacological effects. As a result, it has been found that pyrazolo[1,5-a]pyridine-3-carboxylic acid derivatives represented by the below-described formula (I) have not been reported in publications and have excellent serotonin 3 (5-hydroxytryptamine 3; 5-HT3) receptor antagonism, leading to the completion of the present invention.

In one aspect of the present invention, there is thus provided a pyrazolo[1,5-a]pyridine-3-carboxylic acid derivative represented by the following formula (I):

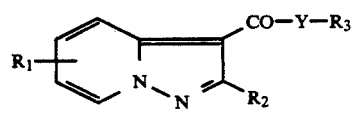

wherein $R_1$ and $R_2$ individually mean a hydrogen atom or a lower alkyl group, $R_3$ denotes an azabicyclo group containing a tertiary nitrogen atom, and Y stands for —O— or —NH—, or a salt thereof.

In another aspect of the present invention, there is also provided a process for the preparation of the pyrazolo[1,5-a]pyridine-3-carboxylic acid derivative (I) or a salt thereof.

In a further aspect of the present invention, there is also provided a serotonin 3 receptor antagonist comprising as an active ingredient the pyrazolo[1,5-a]pyridine-3-carboxylic acid derivative (I) or a salt thereof.

Compounds (I) according to the present invention have excellent serotonin 3 receptor antagonism so that they can be advantageously used as antiemetics, especially as antiemetics for reducing nausea and vomiting due to side effects of a carcinostatic agent. In addition, they can also be advantageously used as gastrointestinal function regulators and phychotropics such as antianxietics.

DETAILED DESCRIPTION OF THE INVENTION AND PREFERRED EMBODIMENTS

Examples of the lower alkyl group represented by $R_1$ and $R_2$ in the pyrazolo[1,5-a]pyridine-3-carboxylic acid derivative (I) of the present invention include linear or branched alkyl groups having 1–5 carbon atoms. Methyl, ethyl or propyl group is preferred as a lower alkyl group. As to the site of substitution, a 7-substituted derivative is especially preferred. However, the unsubstituted derivative and di-substituted derivatives are also preferred. On the other hand, $R_3$ designates an azabicyclo group containing a tertiary nitrogen atom. As the azabicyclo group, a saturated azabicyclo alkyl group is more preferred. Examples of the azabicyclo group include quinuclidyl, 8-methyl-8azabicyclo-[3.2.1]octyl, 9-methyl-9-azabicyclo[3.3.1]-nonyl and the like. Quinuclidyl-containing pyrazolo[1,5-a]pyridine-3-carboxylic acid derivatives (I) are especially preferred. The quinuclidyl group may be either in the racemic form or in an optically active form, with the S-form being particularly preferred. In 8-methyl-8-azabicyclo[3.2.1]octyl- and 9-methyl-9-azabicyclo[3.3.1]nonyl-containing pyrazolo[1,5-a]pyridine3-carboxylic acid derivatives (1), their endo-forms are preferred. Y stands for —O— or —NH—. Compounds in which Y is —O— generally have superior affinity with serotonin 3 receptors. In the body, compounds in which Y is —NH— are however more resistant to hydrolysis and are hence advantageous.

The pyrazolo[1,5-a]pyridine-3-carboxylic acid derivative (I) according to the present invention can be obtained by reacting a pyrazolo[1,5-a]pyridine-3-carboxylic acid compound (II) or its reactive derivative with an azabicyclo compound (III) in accordance with the following formula:

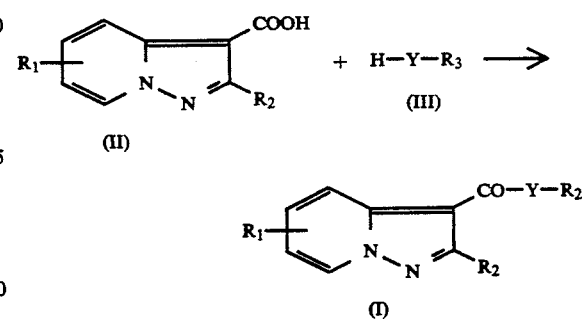

wherein $R_1$, $R_2$, $R_3$ and Y have the same meanings as defined above.

The reaction between the pyrazolo[1,5-a]pyridine-3-carboxylic acid compound (II) or its reactive derivative and the azabicyclo compound (III) can be practiced in accordance with a known esterification or amidation reaction.

Illustrative reactive derivatives of the pyrazolo[1,5-a]pyridine-3-carboxylic acid compound (II) include acid halides, acid anhydrides, acid azides, active esters, active amides and the like. Preferred examples include mixed acid anhydrides with acid chlorides, acid bromides, acetic acid, pivalic acid, isovaleric acid, trichloroacetic acid, monoalkyl carbonates and the like; active esters such as the p-nitrophenyl ester, 2,4-dinitrophenyl ester, trichlorophenyl ester, pentachlorphenyl ester, 1-hydroxy-1H-pyridone ester, N-hydroxysuccinimide ester, and N-hydroxyphthalimide ester; and active amides such as pyrazole, imidazole, dimethylpyrazole and benzotriazole.

When the pyrazolo[1,5-a]pyridine-3-carboxylic acid compound (II) is used in the form of a free acid in the above reaction, it is preferred to conduct the reaction in the presence of a coupling agent. Examples of the coupling agent include carbodiimide compounds such as N,N-dicylohexylcarbodiimide, 1-ethyl-3-(3-dimethylaminopropyl)carbodiimide, N-cyclohexyl-N'-morpholinoethylcarbodiimide and N-cyclohexyl-N'-(4-diethylaminocyclohexyl)carbodiimide; reagents such as diphenylphosphorylazide, benzotriazole-N-hydroxytris(dimethylamino)phosphonium hexafluorophosphorus compound and carbonyl diimidazole; and reagent (so-called Bilsmyer's reagents) formed by reacting amide compounds such as N-methylformamide and N,N-dimethylformamide with halogen compounds such as thionyl chloride, phosphorus oxychloride and phosgene. Other coupling agents can also be used.

The reaction making use of an acid halide or acid anhydride out of reactive derivatives usable in the present invention can be conducted in the presence of a neutralization agent. Examples of usable neutralization agents include organic or inorganic bases such as triethylamine, tributylamine, ethyldiisopropylamine, N,N-dimethylaniline, N-methylmorpholine and pyridine.

The amount ratio of the pyrazolo[1,5-a]pyridine-3-carboxylic acid compound (II) or its reactive derivative to the azabicyclo compound (III) may theoretically be the equimolar ratio, but the azabicyclo compound (III) is excessively used in general. The amount of the azabicyclo compound (III), however, may be up to about 5 molar times at most.

The above reaction is usually conducted in a solvent which does not give adverse effects on the reaction. Examples of the solvent include chloroform, methylene chloride, tetrahydrofuran, dioxane, dimethylformamide, dimethylacetamide and acetone and mixtures thereof.

No particular limitation is imposed on the reaction temperature. In general, the reaction sufficiently proceeds at room temperature. The reaction time varies depending on the reaction temperature, the reactivity of the pyrazolo[1,5-a]pyridine-3-carboxylic acid compound (II) and the kind of reactive derivative and the reactivity of the azabicyclo compound (III). The reaction time, however, may be up to about 24 hours at most.

Of the starting raw materials, the pyrazolo[1,5-a]pyridine-3-carboxylic acid compound (II) is a known compound or can be easily prepared from another known compound. For example, 4- and 6-(lower alkyl)-substituted derivatives can be prepared in accordance with the process disclosed in "Journal of Chemical Society, Perkin Trans Actions Part I (J.C.S. PerkinI)", 406–409 (1975); 5-(lower alkyl)-substituted derivatives in accordance with the process disclosed in "J. C. S. PerkinI", 2580–2583 (1973); unsubstituted and 7-(lower alkyl)-substituted derivatives in accordance with the process disclosed in "The Journal of Organic Chemistry", 33(5), 2062–2064 (1968); and 2,7-di(lower alkyl)-substituted derivatives in accordance with the process disclosed in "YAKUGAKU ZASSHI", 91(11), 1154–1157 (1971).

On the other hand, examples of the azabicyclo compound (III) employed in the above reaction include compounds represented by the following formula (IV):

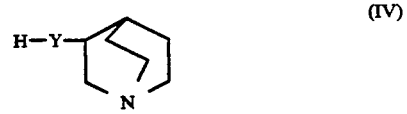

wherein Y has the same meaning as defined above and compounds represented by the following formula (V):

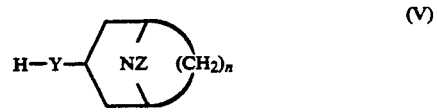

wherein Y, Z and n have the same meanings as defined above. Specific examples of the compounds (V) include 8-methyl-8-azabicyclo[3.2.1]octan-3-ol, 8-methyl-8-azabicyclo[3.2.1.]octan-3-amine, and 9-methyl-9-azabicyclo[3.3.1]nonan-3-amine. Of these, those having an endo form structure are preferred. Also, the reactive derivative of the azabicyclo compound (III) can be used for the preparation of inventive compound (I).

Among these, for example, 3-aminoquinuclidine, 3-quinuclidinol and endo-8-methyl-8-azabicyclo[3.2.1]-octan-3-ol (tropine) are listed in reagent makers' catalogues and are readily available. Further, endo-8-methyl-8-azabicyclo[3.2.1]octan-3-amine and endo-9-methyl-9-azabicyclo[3.2.1]nonan-3-amine are also known compounds and can be prepared by the processes disclosed in "Journal of American Chemical Society (J. Am. Chem. Soc.)", 79, 4194 (1957) and European Patent Application No. (EP) 13,138 (1979), respectively.

In addition, (S)-3-aminoquinuclidine and (R)-3-aminoquinuclidine can be prepared by the process disclosed in Japanese Patent Application Laid-Open No. 196583/1988 (corresponding to Ep 280,603) whereas (S)-3-quinuclidinol and (R)-3-quinuclidinol can be obtained following the process disclosed in "European Journal of Medicinal Chemistry (Eur. J. Med. Chem.)", 14, 111–114 (1979).

The compounds (I) of the present invention prepared in the manner described above can be purified further by a known purification method, for example, column chromatography or recrystallization.

Further, the so-obtained compounds (I) of this invention can be converted to pharmaceutically-acceptable, non-toxic salts as needed.

Examples of such salts include inorganic acid salts such as hydrochlorides, sulfates and phosphates; and organic acid salts such as acetates, propionates, tartrates, citrates, glycolates, gluconates, succinates, malates, glutamates, aspartates and methanesulfonates.

As is clear from the fact that no case of death was observed on any of the compounds (I) of this invention when these mice were each intravenously administered at 30 mg/kg, the compounds (I) can be considered safe when used as drugs.

To use the compounds of the present invention as drugs, it is only necessary to formulate them into dosable preparations and then to administer the preparations, in general, either orally or parenterally, for example, by injection including drip infusion. Their dosage varies depending on the administration route and the age, body weight and conditions of each patient but is generally about 0.1–100 mg/kg per day and adult.

Examples of preparation forms include tablets, pills, powders, granules, capsules, injections and the like. Employed to formulate such preparations, e.g., oral preparations such as tablets, granules and capsules include various carriers corresponding to these preparations, for example, excipients such as starch, lactose, sucrose, mannitol, caboxymethylcellulose, corn starch and inorganic salts; binders such as starch, dextrin, gum arabic, gelatin, hydroxypropylstarch, methylcellulose, sodium carboxymethylcellulose, hydroxypropylcellulose, crystalline cellulose, ethylcellulose, polyvinylpyrrolidone and macrogol; disintegrator such as starch, hydroxypropylstarch, carboxymethylcellulose, sodium carboxymethylcellulose and hydroxypropylcellulose; surfactants such as sodium laurylsulfates, soybean lecithin, sucrose fatty acid esters and polysorbate 80; lubricants such as talc, wax, hydrogenated vegetable oil, sucrose fatty acid esters, magnesium stearate and calcium stearate; fluidity improvers; corrigents; colorants; perfumes; etc.

The compounds (I) or their salts, which pertain to the present invention, can also be used as suspensions, emulsions, syrups, and elixirs.

Parenteral preparations can generally use injection-grade distilled water, physiological saline, aqueous glucose solution, injection-grade vegetable oil, propylene glycol, polyethylene glycol and the like. Antiseptics, stabilizers, isotonicities, soothing agents and the like can also be added as needed.

The present invention will hereinafter be described in further detail by the following examples and tests.

EXAMPLE 1

Synthesis of N-(1-azabicyclo[2.2.2]oct-3-yl)-3-pyrazolo[1,5-a]pyridinecarboxamide [N-(3-quinuclidinyl)-3-pyrazolo[1,5-a]pyridinecarboxamide]

One gram of 3-aminoquinuclidine dihydrochloride (product of Janssen Pharmaceuticals) was neutralized with 5N aq. NaOH solution, followed by extraction with chloroform. After the chloroform solution was dried over $Na_2SO_4$, chloroform was distilled off.

On the other hand, 3 ml of $SOCl_2$ were added to 0.27 g (1.7 mmol) of 3-pyrazolo[1,5-a]pyridinecarboxylic acid which had been prepared in accordance with "The Journal of Organic Chemistry", 33(5), 2062–2064 (1968), and the resulting mixture was heated under reflux for 30 minutes. After excess $SOCl_2$ was distilled off, a solution of the aforementioned 3-aminoquinuclidine in 5 ml of chloroform was added to the residue under ice cooling, followed by stirring at room temperature for 12 hours. 2N HCl was added to the reaction mixture, the hydrochloric acid layer was made alkaline with $Na_2CO_3$, water was distilled off, and the residue was extracted with chloroform. After the chloroform solution was dried over $Na_2SO_4$, the solvent was distilled off and the residue was subjected to chromatography on a silica gel column, whereby 0.4 g of the title compound was obtained from chloroformmethanol (20:1 ) eluate fractions (yield: 88%).

The compound obtained above was dissolved in dry benzene, which HCl gas introduced under ice cooling. Precipitated crystals were collected by suction filtration and then recrystallized from benzene-methanol, whereby N-(3-quinuclidinyl)-3-pyrazolo[1,5-a]pyridine carboxamide hydrochloride was obtained. MS(m/z): 270

REFERENTIAL EXAMPLE 1

Synthesis of 5-methylpyrazolo[1,5-a]pyridine-3-carboxylic acid

To 1.00 g (4.9 mmol) of ethyl 5-methylpyrazolo[1,5-a]pyridine-3-carboxylate prepared by the process disclosed in "J. C. S. PerkinI", 2580–2583 (1973), 10 ml of 5N aq. NaOH solution and 3 ml of methanol were added, followed by stirring at room temperature for 24 hours. After the reaction, the solvents were distilled off and the residue was dissolved in water. The aqueous solution was washed with benzene. The water layer was made acidic with concentrated hydrochloric acid, and crystals precipitated were collected by filtration and then washed with water. Yield: 0.60 g (3.4 mmol) (70%).

Melting point: 232°–234° C.

Elemental analysis (as $C_9H_8N_2O_2$): Calculated: C, 61.36; H, 4.58; N, 15.90. Found: C, 61.11; H, 4.57; N, 15.78.

IR $\nu$max cm$^{-1}$(KBr): 1654 (C=O).

EXAMPLE 2

Synthesis of 5-methyl-N-(1-azabicyclo[2.2.2]oct-3-yl)-3-pyrazolo[1,5-a]pyridinecarboxamide [5-methyl-N-(3-quinuclidinyl)-3-pyrazolo[1,5-a]-pyridinecarboxamide]

One gram of 3-aminoquinuclidine dihydrochloride was neutralized with 5N aq. NaOH solution, followed by extraction with chloroform. After the chloroform solution was dried over $Na_2SO_4$, chloroform was distilled off.

On the other hand, 0.2 g of 5-methyl-3pyrazo[ 1,5-a]pyridinecarboxylic acid obtained in Reference Example 1 was dissolved in 3 ml of thionyl chloride, and the resultant solution was refluxed for 30 minutes. After thionyl chloride was distilled off, the above-mentioned 3-aminoquinuclidine was added to the thus-obtained acid chloride. The mixture so obtained was stirred for 24 hours in 5 ml of chloroform. The reaction mixture was extracted with 2N aq. HCl solution, the hydrochloric acid layer was made alkaline with $Na_2CO_3$, and water was then distilled off. The residue was extracted with chloroform, the extract was dried over $Na_2SO_4$, and chloroform was distilled off. The residue was subjected to chromatography on a silica gel column, whereby 0.15 g of the title compound was obtained from chloroform-methanol (20:1) eluate fractions (yield: 47.1%).

Melting point: 100°–102° C.

EXAMPLE 3

Synthesis of 6-methyl-N-(1-azabicyclo[2.2.2]oct-3-yl)-3-pyrazolo[1,5-a]pyridinecarboxamide [6-methyl-N-(3-quinuclidinyl)-3-pyrazolo[1,5-a]-pyridinecarboxamide]

3-Aminoquinuclidine dihydrochloride (0.9 g) was neutralized with aq. NaOH solution, followed by extraction with chloroform. After the chloroform solution was dried, chloroform was distilled off.

On the other hand, 0.18 g of 6-methyl-3-pyrazolo-[1,5-a]pyridinecarboxylic acid prepared in accordance with "J. C. S. PerkinI", 406–409 (1975) was dissolved in 2.7 ml of thionyl chloride. The resultant solution was refluxed for 30 minutes. After thionyl chloride was distilled off, the above-mentioned 3-aminoquinuclidine was added to the resultant acid chloride. The mixture so obtained was stirred for 24 hours in 5 ml of chloroform.

The reaction mixture was extracted with 2N HCl, the hydrochloric acid layer was made alkaline with Na₂CO₃, and water was then distilled off. The residue was extracted with chloroform, the extract was dried over Na₂SO₄, and chloroform was distilled off. The residue was subjected to chromatography on a silica gel column, whereby 0.15 g of the title compound was obtained from chloroform-methanol (20:1) eluate fractions (yield: 54.4%).

Melting point: 142°–144° C.

EXAMPLE 4

Synthesis of 7-methyl-N-(1-azabicyclo[2.2.2]oct-3-yl)-3-pyrazolo[1,5-a]pyridinecarboxamide [7-methyl-N-(3-quinuclidinyl)-3-pyrazolo[1,5-a]-pyridinecarboxamide]

One gram of 3-aminoquinuclidine dihydrochloride was neutralized with 5N aq. NaOH solution, followed by extraction with chloroform. After the chloroform solution was dried over Na₂SO₄, chloroform was distilled off.

On the other hand, 0.2 g of 7-methyl-3-pyrazo[1,5-a]pyridinecarboxylic acid prepared in accordance with J. Org. Chem., 33(5), 2062–2064 (1968) was dissolved in 3 ml of thionyl chloride, and the resultant solution was refluxed for 30 minutes. After thionyl chloride was distilled off, the above-mentioned 3-aminoquinuclidine was added to the thus-obtained acid chloride. The mixture so obtained was stirred for 24 hours in 5 ml of chloroform. The reaction mixture was extracted with 2N aq. HCl solution, the hydrochloric acid layer was made alkaline with Na₂CO₃, and water was then distilled off. The residue was extracted with chloroform, the extract was dried over Na₂SO₄, and chloroform was distilled off. The residue was subjected to chromatography on a silica gel column, whereby 0.26 g of the title compound was obtained from chloroform-methanol (20:1) eluate fractions (yield: 82%).

$^1$H-NMR (CDCl₃, CD₃OD) δ ppm: 8.29(1H,s,C²-H),8.19(1H,d,J=8.4 Hz,C⁴-H), 7.31(1H,dd,J=8.4 Hz,J=6.8 Hz,C⁵-H), 6.79(1H,d,J=6.8 Hz,C⁶-H), 4.14–4.28(1H,m,quinuclidine 3-H), 1.46–3.48(11H,m,quinuclidine H), 2.78(3H,s,C⁷-CH₃)

MS(m/e): 284 (M⁺).

IR νmax cm⁻¹(KBr): 1637 (C=O).

Melting point: 198°–200° C.

REFERENTIAL EXAMPLE 2(1)

Synthesis of ethyl 2-methyl-3-pyrazolo[1,5-a]-pyridinecarboxylate

K₂CO₃ (3.0 g, 21.4 mmol) was added to a solution of 2.0 g (9 mmol) of 1-aminopyridinium iodide, which had been prepared in accordance with "Org. Syn.", 1, 43 (1963), in 100 ml of ethanol. The resultant mixture was stirred at room temperature for 30 minutes, followed by the addition of 1.8 g (13.8 mmol) of ethyl acetoacetate. The mixture thus obtained was stirred further for 24 hours. After K₂CO₃ was filtered off, ethanol was distilled off. Water was added to the residue so obtained, followed by extraction with benzene. After benzene was distilled off, the residue was subjected to chromatography on a silica gel column. Crystals obtained from petroleum benzine-benzene (2:1) eluate fractions were recrystallized from petroleum benzine, whereby 0.74 g of the title compound was obtained (yield: 42%).

Melting point: 93°–94° C.

REFERENTIAL EXAMPLE 2(2)

Synthesis of 2-methyl-3-pyrazolo[1,5-a]pyridine -carboxylic acid

A small amount of methanol was added to a solution of 0.356 g of ethyl 2-methyl-3-pyrazolo[1,5-a]-pyridinecarboxylate in 10 ml of 5N aq. NaOH solution, followed by stirring at room temperature for 24 hours. The reaction mixture was washed with benzene and then made acidic with concentrated hydrochloric acid. Crystals precipitated were collected by suction filtration. The crystals so obtained were dried and then recrystallized from benzene, whereby 0.16 g of the title compound was obtained (yield: 52.4%).

Melting point: 235°–237° C (decomposed).

EXAMPLE 5

Synthesis of 2-methyl-N-(1-azabicyclo[2.2.2]oct-3-yl)-3-pyrazolo[1,5-a]pyridinecarboxamide [2-methyl-N-(3-quinuclidinyl)-3-pyrazolo[1,5-a]-pyridinecarboxamide]

3-Aminoquinuclidine dihydrochloride (0.7 g) was neutralized with aq. NaOH solution, followed by extraction with chloroform. After the chloroform solution was dried, chloroform was distilled off.

On the other hand, 0.14 g of 2-methyl-3-pyrazolo[1,5-a]pyridinecarboxylic acid obtained in Referential Example 2(2) was dissolved in 2.1 ml of thionyl chloride. The resultant solution was refluxed for 30 minutes. After thionyl chloride was distilled off, the above-mentioned 3-aminoquinuclidine was added to the resultant acid chloride. The mixture so obtained was stirred for 24 hours in 5 ml of chloroform. The reaction mixture was extracted with 2N HCl, the hydrochloric acid layer was made alkaline with Na₂CO₃, and water was then distilled off. The residue was extracted with chloroform, the extract was dried over Na₂SO₄, and chloroform was distilled off. The residue was subjected to chromatography on a silica gel column, whereby 0.15 g of the title compound was obtained from chloroform-methanol (20:1) eluate fractions (yield: 66,8%).

$^1$H-NMR (CDCl₃, CD₃OD) δ ppm: 8.40(1H,d,J=7.0 Hz,C₇-H), 8.01(1H,d,J=9.2 Hz,C⁴-H), 7.35(1H,dd,J=9.2 Hz,J=6.8 Hz,C⁵-H), 6.89(1H,dd,J=7.0 Hz,j=6.8 Hz,C⁶-H), 4.16–4.28(1H,m,quinuclidine 3-H), 1.55–3.48(11H,m,quinuclidine H), 2.68(3H,s,C²-CH₃).

MS(m/e): 284 (M⁺).

IR νmax cm⁻¹(KBr): 1614 (C=O).

Melting point: 124°–125° C.

EXAMPLE 6

Synthesis of endo-8-methyl-8-azabicyclo[3.2.1]-oct-3-yl pyrazolo[1,5-a]pyridine-3-carboxylate Dissolved in 2 ml of thionyl chloride was 0.2 g of 3-pyrazolo[1,5-a]pyridinecarboxylic acid prepared in accordance with the procedure disclosed in "The Journal of Organic Chemistry", 33(5), 2062–2064 (1968). The resulting solution was refluxed for 1 hour. After thionyl chloride was distilled off, 0.2 g of endo-8-methyl-8-azabicyclo[3.2.1]octan-3-ol (tropine; product of Aldrich Chemical Co., Inc.) was added, followed by overnight reflux in 3.5 ml of chloroform. Water was added under stirring, followed by the addition of Na₂CO₃ to make the solution alkaline. The chloroform layer was distilled and the residue was subjected to chromatography on a silica gel column, whereby 0.09 g of the title compound was obtained as crystals from chloroform-methanol mixed solvent (chloroform:methanol=40:1) eluate fractions (yield: 25.5%).

$^1$H-NMR (CDCl$_3$) δ ppm: 8.50(1H,d,J=7 Hz), 8.25(1H,s), 8.15(1H,d,J=10 Hz), 7.42(1H,dd,J=10 Hz,J=8 Hz), 6.96(1H,dd,J=7 Hz,J=8 Hz), 5.15–5.35(1H,m), 3.10–3.40(2H,m), 2.35(3H,s), 1.50–2.30(8H,m).

MS(m/e): 285 (M+).

IR νmax cm$^{-1}$(KBr): 1692 (C=O).

EXAMPLE 7

Synthesis of endo-8-methyl-8-azabicyclo[3.2.1]-oct-3-yl 7-methylpyrazolo[1,5-a]pyridine-3-carboxylate Dissolved in 4 ml of thionyl chloride was 0.4 g of 7-methyl-3-pyrazolo[1,5-a]pyridinecarboxylic acid prepared in accordance with the procedure disclosed in "The Journal of Organic Chemistry", 3(5), 2062–2064 (1968). The resulting solution was refluxed for 30 minutes. After thionyl chloride was distilled off, 0.32 g of endo-8-methyl-8-azabicyclo[3.2.1]octan-3-ol (product of Aldrich Chemical Co , Inc.) was added, followed by reflux for 24 hours in 5 ml of chloroform. Small amounts of water and 5N aq. NaOH solution were added to make the solution alkaline. The chloroform layer was distilled and the resulting oily substance was subjected to chromatography on a silica gel column, whereby 0.19 g of the title compound was obtained as powder from chloroform-methanol mixed solvent (chloroform:methanol=50:1) eluate fractions (yield: 28%).

$^1$H-NMR (CDCl$_3$) δ ppm: 8.27(1H,s), 8.00(1H,d,J=8.4 Hz), 7.26(1H,dd,J=8.4 Hz,J=7.8 Hz), 6.74( J=7.8 Hz), 4.95–5.43(1H,m), 2.97–3.50(2H,m), 2.76(3H,s), 2.38(3H,s), 1.55–2.65(8H,m).

MS(m/e): 299 (M+).

IR νmax cm$^{-1}$(KBr): 1694 (C=O).

EXAMPLE 8

Synthesis of endo-8-methyl-8-azabicyclo[3.2.1]-oct-3-yl 7-methyl-pyrazolo[1,5-a]pyridine-3-carboxamide Dissolved in 4 ml of thionyl chloride was 0.4 g of 7-methyl-3-pyrazolo[1,5-a]pyridinecarboxylic acid, followed by reflux for 30 minutes. After thionyl chloride was distilled off, 0.56 g of endo-8-methyl-8-azabicyclo[3.2.1]octan-3-amine ["J.Am.Chem.Soc.", 79, 4194 (1957)] and 0.4 g of triethylamine were added, followed by reflux for 24 hours in 7 ml of chloroform. Water and Na$_2$CO$_3$ were added and the chloroform layer was collected. The chloroform layer was dried over Na$_2$SO$_4$. After the solvent was distilled off, the residue was subjected to chromatography on a silica gel column, whereby 0.52 g of the title compound was obtained as powder from chloroform-methanol mixed solvent (chloroform:methanol=30:1) eluate fractions (yield: 76.7%).

$^1$H-NMR (CDCl$_3$) δ ppm: 8.18(1H,d,J=8.4 Hz), 8.13(1H,s), 7.26(1H,dd,J=8.4 Hz,J=7.8 Hz), 6.77(1H,d,J=7.8 Hz), 4.21–4.70(1H,m), 2.95–3.40(2H,m), 2.76(3H,s), 2.36(3H,s), 1.53–2.41(8H,m).

MS(m/e): 298 (M+).

IR νmax cm$^{-1}$(KBr): 1637 (C=O).

EXAMPLE 9

Synthesis of endo-9-methyl-9-azabicyclo[3.3.1]-non-3-yl 7-methyl-pyrazolo[1,5-a]pyridine-3-carboxamide Dissolved in 4 ml of thionyl chloride was 0.4 g of 7-methyl-3-pyrazolo[1,5-a]pyridinecarboxylic acid, followed by reflux for 30 minutes. After thionyl chloride was distilled off, 0.62 g of endo-9-methyl-9-azabicyclo[3.3.1]nonan-3-amine ["Eur. Pat. Appl. EP 13,138 (1979)] and 0.4 g of triethylamine were added, followed by reflux for 24 hours in 7 ml of chloroform. Water and Na$_2$CO$_3$ were added and the chloroform layer was collected. The chloroform layer was dried over Na$_2$SO$_4$. After the solvent was distilled off, the residue was subjected to chromatography on a silica gel column, whereby 0.47 g of the title compound was obtained from chloroform-methanol mixed solvent (chloroform:methanol=30:1) eluate fractions (yield: 66%).

$^1$H-NMR (CDCl$_3$) δ ppm: 8.23(1H,d), 8.16(1H,s), 7.26(1H,dd,J=8.4 Hz,J=7.8 Hz), 6.75(1H,d,J=7.7 Hz), 4.5–4.7(1H,m), 3.10(2H,d), 2.78(3H,s), 2.51(3H,s), 1.0–2.6(10H,m).

MS(m/e) 212 (M+).

IR νmax cm$^{-1}$(KBr) 1636 (C=O).

EXAMPLE 10

Synthesis of (S)-(-)-N-(1-azabicyclo[2.2.2]oct-3-yl)-7-methylpyrazolo[1,5-a]pyridine-3-carboxamide A solution of 880 mg (5 mmol) of 7-methyl-3-pyrazolo[1,5-a]pyridinecarboxylic acid in 10 ml of thionyl chloride was heated under reflux for 30 minutes. Thionyl chloride was distilled off under reduced pressure and the residue was dissolved in 30 ml of methylene chloride. The resultant solution was added dropwise under ice cooling to a solution of 644 mg (5.1 mmol) of (S)-(−)-1-azabicyclo[2.2.2]octan-3-amine, which had been prepared in accordance with the procedure disclosed in Japanese Patent Application Laid-Open No. 196583/1988, in 30 ml of methylene chloride. The resultant mixture was stirred for 30 minutes under ice cooling and for additional 40 minutes at room temperature. 2N aq. NaOH solution was added to the reaction mixture and, after the mixture so obtained was stirred for 10 minutes, the organic layer was collected. Further, the water layer was extracted with methylene chloride and the extract was dried over anhydrous potassium carbonate. Methylene chloride was distilled off under reduced pressure, and the residue was purified by chromatography on a silica gel column (chloroform:methanol=10:1, 5:1). An oily substance thus obtained was dissolved in ethyl acetate. The solvent was distilled off under reduced pressure, and crystals thus obtained were washed with ether, whereby 1.2 g (4.2 mmol) of the title compound were obtained as white crystals (yield: 84.5%).

$^1$H-NMR (CDCl$_3$) δ (ppm): 8.25(1H,s,C$_2$-H), 8.20(1H,d,J=8.9 Hz,C$^4$-H), 7.31(1H,dd,J=8.9 Hz,J=6.9 Hz),C$^5$-H), 6.79(1H,d,J=6.9 Hz,C$^6$-H), 6.12(1H,d,J=6.9 Hz,NH), 4.1–4.3(1H,m,CH), 1.5–3.6(11H,m,quinuclidine-H), 2.78(3H,s,C$_7$-Cu$_3$)

MS: FAB(Pos.) 285(MH+).

$[α]_D^{20}$ = −12.7 (c=1.0, 1N HCl).

EXAMPLE 11

Synthesis of (R)-(+)-N-(1-azabicyclo[2.2.2]oct-3-yl)-7-methylpyrazolo[1,5-a]pyridine-3-carboxamide A solution of 166 mg (0.945 mmol) of 7-methyl-3-pyrazolo[1,5-a]pyridinecarboxylic acid in 3 ml of thionyl chloride was heated under reflux for 30 minutes. Thionyl chloride was distilled off under reduced pressure and the residue was dissolved in 5 ml of methylene chloride. The resultant solution was added dropwise under ice cooling to a solution of 200 mg (1 mmol) of (R)-(+)-1-azabicyclo[2.2.2]octan-3-amine, which had been prepared in accordance with the procedure disclosed in Japanese Patent Application Laid-Open No. 196583/1988, in 5 ml of methylene chloride. The resultant mixture was stirred for 30 minutes under ice cooling and for additional 40 minutes at room temperature. 2N aq. NaOH solution was added to the reaction mixture and, after the mixture so obtained was stirred for 10 minutes, the organic layer was collected. Further, the water layer was extracted with methylene chloride and the extract was dried over anhydrous potassium carbonate. Methylene chloride was distilled off under reduced pressure, and the residue was purified by chromatography on a silica gel column (chloroform:methanol=10:1, 5:1). An oily substance thus obtained was dissolved in ethyl acetate. The solvent was distilled off under reduced pressure, and crystals thus obtained were washed with ether, whereby 207 mg (0.73 mmol) of the title compound were obtained as white crystals (yield: 77.0%).

$^1$H-NMR (CDCl$_3$) δ (ppm): 8.26(1H,s,C$^2$-H), 8.20(1H,ds,J=8.9 Hz,C$^4$-H), 7.31(1H,dd,J=8.9 Hz,J=6.9 Hz,C$^5$-H), 6.79(1H,d,J=6.9 Hz,C$^6$-H), 6.14(1H,d,J=6.3 Hz,NH), 4.1–4.3(1H,m,CH), 1.5–3.6(11H,m,quinuclidine-H), 2.78(3H,s,C$^7$-CH).

MS: FAB(Pos.) 285 (MH+).

$[α]_D^{20}$ = +13.2 (c=1.0, 1N HCl).

EXAMPLE 12

Synthesis of 1-azabicyclo[2.2.2]oct-3-yl 7-methylpyrazolo[1,5-a]pyridine-3-carboxylate After a suspension of 370 mg (2.9 mmol) of 3-quinuclidinol (product of Aldrich Chemical Co., Inc.) in 30 ml of benzene was refluxed for 1.5 hours by using a Dean-Stark apparatus, 0.1 g of metal sodium was added and the resultant mixture was refluxed under stirring for further 2.5 hours. Unreacted sodium was removed and 200 mg (0.98 mmol) of ethyl 7-methylpyrazolo[1,5-a]pyridine-3-carboxylate were added, followed by heating under reflux for 24 hours. The solvent of the reaction mixture was distilled off under reduced pressure and the residue was purified by chromatography on a silica gel column (chloroform: methanol=10:1), whereby 240 mg (0.84 mmol) of the title compound were obtained as white crystals (yield: 86%).

$^1$H-NMR (CDCl$_3$) δ (ppm): 8.45(1H,s,C$^2$-H), 8.06(1H,d,J=8.9 Hz,C$^4$-H), 7.38(1H,dd,J=8.9 Hz,J=6.9 Hz,C$^5$-H), 6.83(1H,d,J=6.9 Hz,C$_6$-H), 5.0–5.1(1H,m,CH), 1.4–3.5(11H,m,quinuclidine-H), 2.80(3H,s,CH$_3$)

MS: FAB(Pos.) 286 (MH+).

EXAMPLE 13

Synthesis of (S)-(-)-1-azabicyclo[2.2.2]oct-3-yl 7-methylpyrazolo[1,5-a]pyridine-3-carboxylate After a suspension of 760 mg (0.76 mmol) of (S)-(+)-3-quinuclidinol, which had been prepared in accordance with the procedure disclosed in "Eur. J. Med. Chem.", 14, 111–114 (1979), in 60 ml of benzene was refluxed for 1.5 hours by using a Dean-Stark apparatus, 0.2 g of metal sodium was added and the resultant mixture was refluxed under stirring for further 2.5 hours. Unreacted sodium was removed and 440 mg (2.2 mmol) of ethyl 7-methylpyrazolo[1,5-a]pyridine-3-carboxylate were added, followed by heating under reflux for 24 hours. The solvent of the reaction mixture was distilled off under reduced pressure and the residue was purified by chromatography on a silica gel column (chloroform:methanol=10:1), whereby 500 mg (1.8 mmol) of the title compound were obtained as white crystals (yield: 81%).

$^1$H-NMR (CDCl$_3$) δ (ppm): 8.45(1H,s,C$^2$-H), 8.06(1H,d,J=8.9 Hz,C$^4$-H), 7.38(1H,dd,J=8.9HZ,J=6.9 Hz,C$^5$-H), 6.83(1H,d,J=6.9 Hz,C$^6$-H), 5.0–5.1(1H,m,CH), 1.4–3.5(11H,m,quinuclidine-H), 2.81(3H,s,CH$_3$)

MS: FAB(Pos.) 286 (MH+).

$[α]_D^{20}$ = −21.5 (c=1.0, chloroform).

EXAMPLE 14

Synthesis of (R)-(+)-1-azabicyclo[2.2.2]oct-3-yl 7-methylpyrazolo[1,5-a]pyridine-3-carboxylate After a suspension of 90 mg (0.71 mmol) of (R)-(-)-3-quinuclidinol, which had been prepared in accordance with the procedure disclosed in "Eur. J. Med. Chem.", 14, 111–114 (1979), in 15 ml of benzene was refluxed for 1.5 hours by using a Dean-Stark apparatus, 0.05 g of metal sodium was added and the resultant mixture was refluxed under stirring for further 2.5 hours. Unreacted sodium was removed and 100 mg (0.49 mmol) of ethyl 7-methylpyrazolo[1,5-a]pyridine-3-carboxylate were added, followed by heating under reflux for 24 hours. The solvent of the reaction mixture was distilled off under reduced pressure and the residue was purified by chromatography on a silica gel column (chloroform:methanol=10:1), whereby 15 mg (0.05 mmol) of the title compound were obtained as white crystals (yield: 12%).

$^1$H-NMR (CDCl$_3$) δ (ppm): 8.45(1H,s,C$^2$-H), 8.06(1H,d,J=8.9 Hz,C$^4$-H), 7.38(1H,dd,J=8.9 Hz,J=6.9 Hz,C$^5$-H), 6 83(1H,d,J=6.9 Hz,C$^6$-H), 5.0–5.1(1H,m,CH), 1.4–3.5(11H,m,quinuclidine-H), 2.81(3H,s,CH$_3$).

MS FAB(Pos.) 286 (MH+).

$[α]_D^{20}$ = +20.8 (c=1.0, chloroform).

EXAMPLE 15

Synthesis of endo-8-methyl-8-azabicyclo[3.2.1]-oct-3-yl 2-methyl-pyrazolo[1,5-a]pyridine-3-carboxylate Dissolved in 5 ml of thionyl chloride was 0.5 g (3 mmol) of 2-methylpyrazolo[1,5-a]pyridine-3-carboxylic acid, followed by reflux for 30 minutes. After thionyl chloride was distilled off, 6 ml of distilled chloroform were added, followed by the further addition of 0.4 g (3 mmol) of tropine. The resultant mixture was stirred for 24 hours. 5N aq. NaOH solution (2 ml) was added and the mixture thus obtained was stirred for 30 minutes. Water was then added to the reaction mixture and the aqueous mixture so formed was allowed to separate into two layers. The chloroform layer was dried over anhydrous sodium sulfate and the solvent was then distilled off. An oily substance which remained was purified by chromatography on a silica gel column, whereby crystals were obtained from chloroform:methanol=50:1 eluate fractions. The crystals were recrystallized from benzene-methanol, whereby 0.27 g (0.90 mmol) of the title compound was obtained as crystals (yield: 30%).

Melting point: 253°–257° C.

$^1$H-NMR (CDCl$_3$) δ ppm: 8.37(1H,d,J=7.2 Hz,C$^7$-H), 8.07(1H,d,J=8.4 Hz,C$^4$-H), 7.33(1H,dd,J=7.8 Hz,J=8.4 Hz,C$^5$-H), 6.83(1H,dd,J=7.2 Hz,J=7.8 Hz,C$^6$-H), 5.0–5.5(1H,m,tropine 3-H), 2.9–3.6(2H,m,-tropine 1,5-H), 2.71(3H,s,C$^2$–CH$_3$), 2.40(3H,s,tropine N-CH$_3$), 1.5–2.6(8H,m,tropine,H).

MS(m/e): 299 (M+)

IR νmax cm$^{-1}$(KBr): 1685 (C=O).

EXAMPLE 16

Synthesis of endo-8-methyl-8-azabicyclo[3.2.1]-oct-3-yl 4-methyl-pyrazolo[1,5-a]pyridine-3-carboxylate Dissolved in 5 ml of thionyl chloride was 0.5 g (3 mmol) of 4-methylpyrazolo[1,5-a]pyridine-3-carboxylic acid prepared in accordance with the procedure disclosed in "Journal of Chemical Society, Perkin Trans Actions, Part I (J. C. S. PerkinI)" 406–409 (1975), followed by reflux for 30 minutes. After the solvent was distilled off, 6 ml of distilled chloroform were added, followed by the further addition of 0.4 g (3 mmol) of tropine. The resultant mixture was stirred for 24 hours. 5N aq. NaOH solution (2 ml) was added and the mixture thus obtained was stirred for 30 minutes. Water was then added to the reaction mixture and the aqueous mixture so formed was allowed to separate into two layers. The chloroform layer was dried over anhydrous sodium sulfate and the solvent was then distilled off. An oily substance which remained was purified by chromatography on a silica gel column, whereby crystals were obtained from chloroform:methanol=50:1 eluate fractions. The crystals were recrystallized from benzene-methanol, whereby 0.27 g (0.90 mmol) of the title compound was obtained as crystals (yield: 30%).

Melting point: 144°–146° C.

$^1$H-NMR (CDCl$_3$) δ ppm: 8.39(1H,d,J=6.0 Hz,C$^7$-H), 8.27(1H,s,C$^2$-H), 7.19(1H,d,J=7.2 Hz,C$^5$-H), 6.88(1H,dd,J=6.0 Hz,J=7.2 Hz,C$^6$-H), 5.1–5.5(1H,m,-tropine 3-H), 3.5–4.1(2H,m,tropine 1,5-H), 2.87(3H,s,C$^4$-CH$_3$), 2.78(3H,s,tropine N-CH$_3$), 2.1–2.8(8H,m,tropine,H).

MS(m/e): 299 (M+)

IR νmax cm$^{-1}$(KBr): 1705 (C=O).

EXAMPLE 17

Synthesis of endo-8-methyl-8-azabicyclo[3.2.1]-oct-3-yl 5-methylpyrazolo[1,5-a]pyridine-3-carboxylate Dissolved in 5 ml of thionyl chloride was 0.5 g (3 mmol) of 5-methylpyrazolo[1,5-a]pyridine-3-carboxylic acid, followed by reflux for 30 minutes. After thionyl chloride was distilled off, 0.4 g (3 mmol) of tropine was added, followed by reflux for 24 hours in 6.3 ml of chloroform. Small amounts of water and 5N aq. NaOH solution were added to make the solution alkaline. The chloroform layer was distilled. An oily substance which remained was purified by chromatography on a silica gel column (chloroform: methanol=20.1), whereby 0.11 g (0.37 mmol) of the title compound was obtained (yield: 12.3%).

MS(m/e): 299 (M+).

$^1$H-NMR (CDCl$_3$) δ ppm: 8.30(1H,d,J=6 Hz,C$^7$-H), 8.08(1H,s,C$^2$-H), 7.84(1H,s,C$^4$-H), 6.72(1H,d,J=6 Hz,C$^6$-H) 5.13–5.47(1H,m,tropine 3-H), 3.63–4.00(2H,m,tropine 1,5-H), 2.80(3H,s,C$^5$-CH$_3$), 2.44(3H,s,N-CH$_3$), 1.89–2.56(3H,m,tropine H)

EXAMPLE 18

Synthesis of endo-8-methyl-8-azabicyclo[3.2.1]-oct-3-yl 6-methylpyrazolo[1,5-a]pyridine-3-carboxylate Dissolved in 6 ml of thionyl chloride was 0.6 g (3 mmol) of 6-methylpyrazolo[1,5-a]pyridine-3-carboxylic acid, followed by reflux for 30 minutes. After the solvent was distilled off, 7 ml of distilled chloroform were added, followed by the addition of 0.4 g (0.003 mmol) of tropine. The resultant mixture was stirred for 24 hours. 5N aq. NaOH solution (2 ml) was added, followed by stirring for 30 minutes. Water was then added to the reaction mixture and the aqueous mixture so formed was allowed to separate into two layers. The chloroform layer was dried over anhydrous sodium sulfate and the solvent was then distilled off. An oily substance which remained was purified by chromatography on a silica gel column, whereby 0.13 g of the title compound was obtained as crystals from chloroform:methanol=50:1 eluate fractions (yield: 13%).

$^1$H-NMR (CDCl$_3$) δ ppm: 8.33(1H,s,C$^7$-H), 8.26(1H,s,C$^2$-H), 8.06(1H,d,J=7.8 Hz,C$^4$-H), 7.21(1H,d,J=7.8 Hz,C$^5$-H), 5.08–5.50(1H,m,tropine 3-H), 3.10–3.64(2H,m,tropine 1,5-H), 2.48(3H,s,C$^6$-CH$_3$), 2.36(3H,s,tropine N-CH$_3$), 1.68–2.43(8H,m,-tropine,H).

MS(m/e) 299 (M+)

REFERENTIAL EXAMPLE 3

Synthesis of 2,7-dimethylpyrazolo[1,5-a]pyridine-3-carboxylic acid

To 1.00 g (4.6 mmol) of ethyl 2,7-dimethyl-pyrazolo[1,5-a]pyridine-3-carboxylate prepared in accordance with the procedure disclosed in "YAKUGAKU ZASSHI", 91(11), 1154–1157 (1971), 5 ml of 3N aq. NaOH solution and 2 ml of ethanol were added, followed by stirring at 100° C. for 8 hours. After the reaction, the solvents were distilled off, and the residue was dissolved in water and then washed with benzene. The aqueous layer was made acidic with concentrated hydrochloric acid. Crystals precipitated were collected by filtration and then washed with water. Yield: 0.85 g (4.5 mmol) (97%).

$^1$H-NMR (CDCl$_3$) δ ppm: 2.76(s,3H), 2.78(s,3H), 6.78(d,1H,J=6.9 Hz), 7.35(dd,1H,J=8.9 Hz,J=6.9 Hz), 8.09(d,1H,J=8.9 Hz)

EXAMPLE 19

Synthesis of N-(1-azabicyclo[2.2.2]-oct-3-yl-2,7-dimethylpyrazolo[1,5-a]pyridine-3-carboxamide A solution of 200 mg (1.1 mmol) of 2,7-dimethyl-3-pyrazolo[1,5-a]pyridinecarboxylic acid, which had been obtained in Referential Example 3, in 5 ml of thionyl chloride was heated under reflux for 30 minutes. Thionyl chloride was distilled off under reduced pressure and the residue was dissolved in 5 ml of methylene chloride. The resultant solution was added dropwise under ice cooling to a solution of 140 mg (1.1 mmol) of 1-azabicyclo[2.2.2]oct-3-ylamine in 5 ml of methylene chloride. The resultant mixture was stirred for 30 minutes under ice cooling and for additional 40 minutes at room temperature. 2N aq. NaOH solution was added to the reaction mixture and, after the mixture so obtained was stirred for 10 minutes, the organic layer was collected. Further, the water layer was extracted with methylene chloride and the extract was dried over anhydrous potassium carbonate. Methylene chloride was distilled off under reduced pressure, and the residue was purified by chromatography on a silica gel column (chloroform:methanol=10:1). An oily substance thus obtained was dissolved in ethyl acetate. The solvent was distilled off under reduced pressure, and crystals thus obtained were washed with ether, whereby 170 mg (0.57 mmol) of the title compound were obtained as white crystals (yield: 54%).

$^1$H-NMR (CDCl$_3$) δ (ppm): 7.98(1H,d,J=8.9 Hz,C$^4$-H), 7.26(1H,dd,J=8.9 Hz,J=6.6 Hz,C$^5$-H), 6.71(1H,d,J=6.6 Hz,C$^6$-H), 6 03(1H,d,J=6.6 Hz,NH), 4.2–4.3(1H,m,CH), 1.5–3.6(11H,m,quinuclidine-H), 2.74(3H,s,CH$_3$), 2.73(3H,s,CH$_3$).

MS: FAB(Pos.) 299 (MH+).

EXAMPLE 20

Synthesis of 1-azabicyclo[2.2.2]oct-3-yl 2,7-dimethylpyrazolo[1,5-a]pyridine-3-carboxylate After a suspension of 350 mg (2.76 mmol) of 3-quinuclidinol in 30 ml of benzene was refluxed for 1.0 hours by using a Dean-Stark apparatus, 0.1 g of metal sodium was added and the resultant mixture was refluxed under stirring for further 3 hours. Unreacted sodium was removed and 200 mg (0.92 mmol) of ethyl 2,7-dimethylpyrazolo[1,5-a]pyridine-3-carboxylate were added, followed by heating under reflux for 24 hours. The solvent of the reaction mixture was distilled off under reduced pressure and the residue was purified by chromatography on a silica gel column (chloroform: methanol=10:1), whereby 60 mg (0.20 mmol) of the title compound were obtained as white crystals (yield: 22%).

$^1$H-NMR (CDCl$_3$) δ (ppm): 8.01(1H,d,J=8.9 Hz,C$^4$-H), 7.33(1H,dd,J=8.9 Hz,J=6.9 Hz,C$^5$-H), 6.76(1H,d,J=6.9 Hz,C$^6$-H), 5.0–5.1(1H,m,CH), 1.4–3.5(l$^1$H,m,quinuclidine-H), 2.77(3H,s,CH$_3$), 2.73(3H,s,CH$_3$).

MS: FAB(Pos.) 300 (MH+).

REFERENTIAL EXAMPLE 4(1)

Synthesis of ethyl 7-ethylpyrazolo[1,5-a]-pyridine-3-carboxylate

To a solution of 5.0 g (37.6 mmol) of hydroxylamine-O-sulfonic acid in 70 ml of water, 12.0 g (112.1 mmol) of 2-ethylpyridine were added. The resultant mixture was heated under reflux and stirring for 12 hours. After the reaction mixture was neutralized with 4.70 g of Na$_2$CO$_3$, water and 2-ethylpyridine were distilled off. The residue was dissolved in ethanol and the insoluble matter was filtered off. After the filtrate was concentrated to 20 ml, 6.0 ml (42.9 mmol) of 57% hydroiodic acid were added and the resultant mixture was left over in a refrigerator. Crude crystals of 1-amino-2-ethylpyridinium iodide precipitated were collected by filtration and then washed with ethanol. Yield: 4.5 g (18.0 mmol) (48%).

Next, 2.2 g (20.8 mmol) of Na$_2$CO$_3$ were added to a solution of 4.5 g (18.0 mmol) of 1-amino-2-ethylpyridinium iodide in 20 ml of DMF, followed by stirring at room temperature for 1 hour. Ethyl propiolate (3.6 g; 36.7 mmol) was added further, followed by stirring at room temperature for 20 hours. The solvent of the reaction mixture was distilled off. Water was added to the residue, followed by extraction with methylene chloride. After the methylene chloride layer was dried over Na$_2$SO$_4$, the solvent was distilled off and the residue was purified by chromatography on a silica gel column, whereby 0.93 g (4.3 mmol) of the title compound was obtained as crystals (yield: 24%–12% in two steps).

$^1$H-NMR (CDCl$_3$) δ ppm: 1.42(t,3H,J=7.6 Hz), 1.44(t,3H,J=7.3 Hz), 3.23(q,2H,J=7.6 Hz), 4.39(q,2H,J=7.3 Hz), 6.81(d,1H,J=7.3 Hz), 7.39(dd,1H,J=8.9 Hz,J=7.3 Hz), 8.08(d,$^1$H,J=8.9 Hz), 8.43(s,1H).

REFERENTIAL EXAMPLE 4(2)

Synthesis of 7-ethylpyrazolo[1,5-a]pyridine-3-carboxylic acid

To 0.40 g (1.83 mmol) of ethyl 7-ethylpyrazolo[1,5-a]pyridine-3-carboxylate, 8 ml of 2.5N aq. NaOH solution and 8 ml of ethanol were added, followed by stirring at 100° C. for 8 hours. After the reaction, post treatments were conducted in a similar manner to the syntheses bf the 5-methyl and 2,7-dimethyl derivatives so that crystals were obtained. Yield: 0.34 g (1.79 mmol) (98%).

$^1$H-NMR (CDCl$_3$) δ ppm: 1.45(t,3H,J=7 6 Hz), 3.25(q,2H,J=7.6 Hz), 6.87(d,1H,J=6.6 Hz), 7.49(dd,1H,J=8.9 Hz,J=6.6 Hz), 8.13(d,1H,J=8.9 Hz), 8.52(s,1H).

EXAMPLE 21

Synthesis of N-(1-azabicyclo[2.2.2]-oct-3-yl-7-ethylpyrazolo[1,5-a]pyridine-3-carboxamide A solution of 150 mg (0.79 mmol) of 7-ethylpyrazolo[1,5-a]pyridine-3-carboxylic acid, which had been obtained in Referential Example 4(2), in 4 ml of thionyl chloride was heated under reflux for 30 minutes. Thionyl chloride was distilled off under reduced pressure and the residue was dissolved in 5 ml of methylene chloride. The resultant solution was added dropwise under ice cooling to a solution of 100 mg (0.79 mmol) of 1-azabicyclo[2.2.2]-oct-3-ylamine in 5 ml of methylene chloride. The resultant mixture was stirred for 30 minutes under ice cooling and for additional 40 minutes at room temperature. 2N aq. NaOH solution was added to the reaction mixture and, after the mixture so obtained was stirred for 10 minutes, the organic layer was collected. Further, the water layer was extracted with methylene chloride and the extract was dried over anhydrous potassium carbonate. Methylene chloride was distilled off under reduced pressure, and the residue was purified by chromatography on a silica gel column (chloroform:methanol=10:1). An oily substance thus obtained was dissolved in ethyl acetate. The solvent was distilled off under reduced pressure, and crystals thus obtained were washed with ether, whereby 200 mg (0.67 mmol) of the title compound were obtained as white crystals (yield: 85%).

$^1$H-NMR (CDCl$_3$) δ (ppm): 8.38(1H,s,C$^2$-H), 8.19(1H,d,J=8.9 Hz,C$^4$-H), 7.33(1H,dd,J=8.9 Hz,J=6.9 Hz,C$^5$-H), 6.77(1H,d,J=6.9 Hz,C$^6$-H), 6.25(1H,d,J=6.6 Hz,NH), 4.2–4.3(1H,m,CH), 1.5–3.5(11H,m,quinuclidine-H), 3.20(2H,q,J=7.6 Hz,CH$_2$), 1.42(3H,t,J=7.6 Hz,CH$_3$)

MS: FAB(Pos.) 299 (MH+).

REFERENTIAL EXAMPLE 5(1)

Synthesis of ethyl 7-propylpyrazolo[1,5-a]-pyridine-3-carboxylate

To a solution of 9.0 g (67.7 mmol) of hydroxylamine-O-sulfonic acid in 100 ml of water, 25.0 g (206.6 mmol) of 2-n-propylpyridine were added. The resultant mixture was heated under reflux and stirring for 17 hours. After the reaction mixture was neutralized with 8.46 g (79.8 mmol) of Na$_2$CO$_3$, water and 2-n-propylpyridine were distilled off. The residue was dissolved in ethanol and the insoluble matter was filtered off. To the filtrate 11.5 ml (82.1 mmol) of 57% hydroiodic acid were added and the solvent was distilled off. Ether was added to the residue, and the mixture so formed was left over in a refrigerator. Crude crystals of 1-amino-2-propylpyridinium iodide precipitated were collected. Yield: 5.0 g (18.9 mmol) (28%).

Next, 2.41 g (22.7 mmol) of Na$_2$CO$_3$ were added to a solution of 5.0 g (18.9 mmol) of 1-amino-2-propylpyridinium iodide in 20 ml of DMF, followed by stirring at room temperature for 1 hour. Ethyl propiolate (3.71 g; 37.9 mmol) was added further, followed by stirring at room temperature for 20 hours. After the reaction, the reaction mixture was treated in a similar manner to the preparation of the 7-ethyl derivative, whereby 1.45 g (6.25 mmol) of the title compound were obtained as crystals from $CH_2Cl_2$:hexane=1:1 eluate fractions (yield: 33% - 9% in two steps).

1H-NMR ($CDCl_3$) δ ppm: 1.06(t,3H,J=7.4 Hz), 1.42(t,3H,J=7.2 Hz), 1.82–1.96(m,2H), 3.17(t,2H,J=7.6 Hz), 4.39(q,2H,J=7.2 Hz), 6.79(d,1H,J=6.9 Hz), 7.37(dd,1H,J=8.9 Hz,J=6.9 Hz), 8.07(d,1H,J=8.9 Hz), 8.42(s,1H).

REFERENTIAL EXAMPLE 5(2)

Synthesis of 7-propylpyrazolo[1,5-a]pyridine-3-carboxylic acid

To 0 46 g (1.98 mmol) of ethyl 7-propylpyrazolo[1,5-a]pyridine-3-carboxylate, 8 ml of 2.5N aq. NaOH solution and 5 m; of ethanol were added, followed by stirring at 100° C. for 3 hours. After the reaction, post treatments were conducted in a similar manner to the syntheses of the 5-methyl and 2,7-dimethyl derivatives so that 0.37 g (1.81 mmol) of crystals of the title compound were obtained (Yield: 91%).

1H-NMR ($CDCl_3$) δ ppm: 1.07(t,3H,J=7.4 Hz), 1.83–1.97(m,2H), 3.19(t,2H,J=7.6 Hz), 6.84(d,1H,J=6.9 Hz), 7.42(dd,1H,J=8.9 Hz,J=6.9 Hz), 8.12(d,1H,J=8.9 Hz), 8.51(s,1H).

EXAMPLE 22

Synthesis of N-(1-azabicyclo[2.2.2]-oct-3-yl-7-propyl-pyrazolo[1,5-a]pyridine-3-carboxamide A solution of 150 mg (0.74 mmol) of 7-propyl-pyrazolo[1,5-a]pyridinecarboxylic acid, which had been obtained in Referential Example 5(2), in 4 ml of thionyl chloride was heated under reflux for 30 minutes. Thionyl chloride was distilled off under reduced pressure and the residue was dissolved in 5 ml of methylene chloride. The resultant solution was added dropwise under ice cooling to a solution of 110 mg (0.87 mmol) of 1-azabicyclo[2.2.2]-oct-3-ylamine in 5 ml of methylene chloride. The resultant mixture was stirred for 30 minutes under ice cooling and for additional 40 minutes at room temperature. 2N aq. NaOH solution was added to the reaction mixture and, after the mixture so obtained was stirred for 10 minutes, the organic layer was collected. Further, the water layer was extracted with methylene chloride and the extract was dried over anhydrous potassium carbonate. Methylene chloride was distilled off under reduced pressure, and the residue was purified by chromatography on a silica gel column (chloroform: methanol=10:1). An oily substance thus obtained was dissolved in ethyl acetate. The solvent was distilled off under reduced pressure, and crystals thus obtained were washed with ether, whereby 200 mg (0.64 mmol) of the title compound were obtained as white crystals (yield: 87%).

1H-NMR ($CDCl_3$) δ (ppm): 8.37(1H,s,$C^2$-H), 8.9 (1H,d,J=8.3 Hz,$C^4$-H), 7.32(1H,dd,J=8.3 Hz,J=6.6 Hz,$C^5$-H), 6.77(1H,d,J=6.6 Hz,$C^6$-H), 6.49(1H,d,J=6.9 Hz,NH), 4.2–4.3(1H,m,CH), 1.5–3.5(11H,m,quinucli-dine-H), 3.15(2H,t,J=7.7 Hz,$CH_2$), 1.81–1.96(2H,m,$CH_2$), 1.05(3H,t,J=7.4 Hz,$CH_3$)

MS: FAB(Pos.) 299 (MH+).

EXAMPLE 23

Synthesis of 1-azabicyclo[2.2.2]oct-3-yl 7-ethyl-pyrazolo[1,5-a]pyridine-3-carboxylate After suspension of 140 mg (1.10 mmol) of 3-quinuclidinol in 20 ml of benzene was refluxed for 0.5 hour by using a Dean-Stark apparatus, 0.05 g of metal sodium was added and the resultant mixture was refluxed under stirring for further 1.5 hours. Unreacted sodium was removed and 80 mg (0.37 mmol) of ethyl 7-ethyl-pyrazolo[1,5-a]pyridine-3-carboxylate were added, followed by heating under reflux for 12 hours. The solvent of the reaction mixture was distilled off under reduced pressure and the residue was purified by chromatography on a silica gel column (chloroform: methanol=10:1), whereby 100 mg (0.33 mmol) of the title compound were obtained as an oily substance (yield: 91%).

1H-NMR ($CDCl_3$) δ (ppm): 8.44(1H,s,$C^2$-H), 8.05(1H,d,J=8.9 Hz,$C^4$-H), 7.40(1H,dd,J=8.9 Hz,J=7.3 Hz,$C^5$-H), 6.83(1H,d,J=7.3 Hz,$C^6$-H), 5.0–5.1(1H,m,CH), 1.4–3.5(11H,m,quinuclidine-H), 3.23(2H,q,J=7.6 Hz,$CH_2$), 1.44(3H,t,J=7.6 Hz,$CH_3$)

MS: FAB(Pos.) 300 (MH+).

EXAMPLE 24

Synthesis of 1-azabicyclo[2.2.2]oct-3-yl 7-propyl-pyrazolo[1,5-a]pyridine-3-carboxylate After a suspension of 330 mg (2.60 mmol) of 3-quinuclidinol in 30 ml of benzene was refluxed for 0.5 hour by using a Dean-Stark apparatus, 0.1 g of metal sodium was added and the resultant mixture was refluxed under stirring for further 2 hours. Unreacted sodium was removed and 200 mg (0.86 mmol) of ethyl 7-propyl-pyrazolo[1,5-a]pyridine-3-carboxylate were added, followed by heating under reflux for 20 hours. The solvent of the reaction mixture was distilled off under reduced pressure and the residue was purified by chromatography on a silica gel column (chloroform: methanol=10:1), whereby 230 mg (0.73 mmol) of the title compound were obtained as an oily substance (yield: 85%).

1H-NMR ($CDCl_3$) δ (ppm): 8.43(1H,s,$C^2$-H), 8.05(1H,d,J=8.6 Hz,$C^4$-H), 7.39(1H,dd,J=8.6 Hz,J=6.9 Hz,$C^5$-H), 6.81(1H,d,J=6.9 Hz,$C^6$-H), 5.0–5.1(1H,m,CH), 1.4–3.5(11H,m,quinuclidine-H), 3.17(2H,t,J=7.6 Hz,$CH_2$), 1.82–1.96(2H,m,$CH_2$), 1.06(3H,t,J=7.3 Hz,$CH_3$)

MS: FAB(Pos.) 314 (MH+).

Test 1

5-HT$_3$ Receptor Binding Experiment (A) Preparation of rat cerebral cortical membrane fraction:

Subsequent to decapitation of an SD male rat (200–300 g), the brain was promptly taken out. The cerebral cortex was enucleated while immersing the brain under ice cooling in 0.32 M sucrose solution. 50 mM N-2-hydroxyethylpiperazine-N'-2-ethanesulfonate buffer (HEPES), pH 7.4 was then added to the isolated tissue to homogenate the same. The homogenate was centrifuged (1.000×g, 10 min), and the supernatant was centrifuged further (48,000×g, 15 min) to obtain a precipitate. After the precipitate was re-suspended in 0.03% Triton X-100, centrifugation (48,000×g, 15 min) was conducted to obtain a precipitate as a corticocerebral membrane fraction.

(B) $^3$H-quipazine binding assay:

The quantity of $^3$-H-quipazine [product of New England Nuclear Company (NEN); final concentration: 1 nM] reacted with the above-prepared rat corticocerebral membrane fraction (about 200 μg proteins) was designated as a total bound quantity (TB), while the quantity of $^3$-H-quipazine reacted with the rat corticocerebral membrane fraction after adding "ICS 205-930" (product of Research Biochemicals Incorporated; final concentration 100 nM) was designated as a non-specific bound quantity (NB). To investigate the binding activity of each sample, the sample was added to the membrane fraction and $^3$-H-quipazine, followed by the reaction (DTB). The reaction was conducted at 25° C. for 45 minutes, using 1 ml in total. The reaction was terminated by subjecting the reaction mixture to suction filtration through a Watmann GF/C filter. The radioactivity adsorbed on the filter was measured by a liquid scintillation counter. The binding activity of the sample was calculated by the calculation formula which follows to determine it in terms of the rate of inhibition of the binding of $^3$H-quipazine to the 5-HT$_3$ receptor. The results are summarized in Table 1.

(Calculation formula)

$^3$H-quipazine binding inhibitory rate (%) =

$$100 - \frac{DTB - NB}{TB - NB} \times 100$$

TABLE 1

(Results)

| Test compound (Example No.) | Binding inhibitory rate (%) | |
|---|---|---|
| | $10^{-8}$ M | $10^{-9}$ M |
| 1 | 50 | — |
| 2 | 31 | — |
| 4 | 82 | — |
| 5 | 50 | — |
| 6 | 37 | 9 |
| 7 | 77 | 43 |

In addition, the binding inhibitory rate of each compound was determined at desired concentrations. A concentration-binding inhibition curve was then prepared, in which logarithmic values of concentrations were plotted along the axis of abscissas and binding inhibitory rates were plotted along the axis of ordinates. From the curve, the IC$_{50}$ value (the concentration corresponding to 50% inhibition of the binding) of the compound was determined. The results are shown in Table 2.

TABLE 2

| Test compound (Example No.) | IC$_{50}$ value (nM) |
|---|---|
| 1 | 41.1 |
| 2 | 43.2 |
| 4 | 7.2 |
| 5 | 18.9 |
| 6 | 16.5 |
| 7 | 1.0 |
| 8 | 19.1 |
| 9 | 53.7 |
| 10 | 0.28 |
| 11 | 44.9 |
| 12 | 0.21 |
| 13 | 0.11 |
| 14 | 1.3 |
| 15 | 2.7 |
| 16 | 3.5 |
| 17 | 25.8 |
| 19 | 5.2 |
| 20 | 0.14 |
| Control* 1 | — |
| Control* 2 | — |

TABLE 2-continued

| Test compound (Example No.) | IC$_{50}$ value (nM) |
|---|---|
| Control* 3 | — |
| Control* 4 | — |
| Control* 5 | — |
| Control* 6 | — |
| Control* 7 | — |

—: IC$_{50}$ >10,000
Control* 1: Pyrazolo[1,5-a]pyridine-3-carboxylic acid
Control* 2: 2-Methylpyrazolo[1,5-a]pyridine-3-carboxylic acid (obtained in Referential Example 2)
Control* 3: 4-Methylpyrazolo[1,5-a]pyridine-3-carboxylic acid
Control* 4: 5-Methylpyrazolo[1,5-a]pyridine-3-carboxylic acid (obtained in Referential Example 1)
Control* 5: 6-Methylpyrazolo[1,5-a]pyridine-3-carboxylic acid
Control* 6: 7-Methylpyrazolo[1,5-a]pyridine-3-carboxylic acid
Control* 7: 2,7-Dimethylpyrazolo[1,5-a]pyridine-3-carboxylic acid (obtained in Referential Example 3)

Test 2

Antiemetic Effects

Using four 9-13 month-old female beagles having a body weight of 7.5-9.6 Kg (furnished by Toyo Research Animal Inc.), the antiemetic effects of certain compounds of the present invention were investigated.

As test compounds, the compounds obtained in Examples 8 and 9, respectively, were individually weighed and dissolved in 0.01N hydrochloric acid. The resultant solutions were neutralized to about pH 7 with 0.01N NaOH to provide aqueous solutions for administration. Cisplatin ("Briplatin Injection", product of Bristol-Myers Co.) was used as an emetic.

To see the emetic effects of cisplatin to each animal, vomiting after the administration of cisplatin was first observed (control group). Next, seven weeks later, each group consisting of two beagles was intravenously administered with 0.1 mg/kg (0.2 ml/kg) of the compound of Example 8 or 9 upon an elapsed time of 75 minutes after the administration of cisplatin, and the group administered with the compound of Example 8 and the group administered with the compound of Example 9 were both observed for vomit. Cisplatin was intravenously administered at the dosage of 3 mg/kg (in the volume of 6 ml/kg) and the administration rate of 10 ml/min.

The laboratory animals were fasted for about 24 hours prior to administration of cisplatin and, one hour after the administration of cisplatin, were fed. Vomit was determined depending on whether vomitus was discharged out of the mouth. With respect to the number of vomits and their latency, observation was continued for 4 hours after the administration of cisplatin.

Based on the observation, the latency of the first vomit of and the number of vomits of each laboratory animal after the administration of cisplatin are shown in Table 3-A and Table 3-B.

TABLE 3-A

| Antiemetic Effects of the Compound of Example 8 | | | |
|---|---|---|---|
| | Dog No. | Control group | Group administered with test compound |
| Latency of the first vomit (minutes) | 1 | 126 | — |
| | 2 | 114 | — |
| Number of vomits (times) | 1 | 13 | 0 |
| | 2 | 22 | 0 |

TABLE 3-B
Antiemetic Effects of the Compound of Example 9

|  | Dog No. | Control group | Group administered with test compound |
|---|---|---|---|
| Latency of the first vomit (minutes) | 3 | 106 | 132 |
|  | 4 | 98 | 173 |
| Number of vomits (times) | 3 | 12 | 12 |
|  | 4 | 27 | 10 |

According to Table 3-A which shows the results of the administration test of the compound of Example 8, the latencies of the first vomit by the beagles in the control group not administered with the test compound were 126 minutes and 114 minutes, respectively, and the numbers of vomits were 13 times and 22 times, respectively. No vomit was, however, observed on any of the two beagles by the administration of the compound of Example 8 at 0.1 mg/kg, whereby antiemetic effects were confirmed.

Further, in Table 3-B which shows the results of the administration test of the compound of Example 9, the latencies of the first vomit in the control group were 106 minutes and 98 minutes, respectively, and the numbers of vomits were 12 times and 27 times, respectively. The administration of the compound of Example 9 at 0.1 mg/kg prolonged the latencies of the first vomit to 132 minutes and 173 minutes, respectively. The numbers of vomits were 12 times and 27 times, respectively. The number of vomits therefore decreased in one case.

We claim:

1. A serotonin 3 receptor antagonist comprising as an active ingredient a pyrazolo[1,5-a]pyridine-3-carboxylic acid derivative represented by the following formula (I):

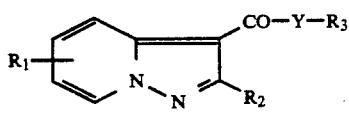

wherein $R_1$ and $R_2$ individually mean a hydrogen atom or a lower alkyl group, $R_3$ denotes a group represented by the following formula:

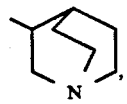

and Y stands for —O— or —NH—, or a salt thereof, and a pharmaceutically acceptable diluent.

2. A serotonin 3 receptor antagonist comprising as an active ingredient a pyrazolo[1,5-a]pyridine-3-carboxylic acid derivative represented by the following formula (I):

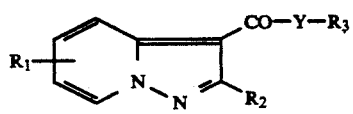

wherein $R_1$ and $R_2$ individually mean a hydrogen atom or a lower alkyl group, $R_3$ denotes a group represented by the following formula:

wherein Z means a lower alkyl group and n stands for an integer of 2 or 3, and Y stands for —O— or —NH—, or a salt thereof, and a pharmaceutically acceptable diluent.

3. The derivative or salt of claim 5, which is a compound selected from the group consisting of optically active or racemic N-(1-azabicyclo[2.2.2]oct-3-yl)-pyrazolo[1,5-a]pyridine-3-carboxamide, N-(1-azabicyclo[2.2.2]oct-3-yl)-5-methylpyrazolo[1,5-a]pyridine-3-carboxamide, N-(1-azabicyclo[2.2.2]oct-3-yl)-7-methylpyrazolo[1,5-a]pyridine-3-carboxamide, N-(1-azabicyclo[2.2.2]oct-3-yl)-2-methylpyrazolo[1,5-a]pyridine-3-carboxamide, N-(1-azabicyclo[2.2.2]oct-3-yl)-2,7-dimethylpyrazolo[1,5-a]pyridine-3-carboxamide, N-(1-azabicyclo[2.2.2]oct-3-yl)-7-ethylpyrazolo[1,5-a]-pyridine-3-carboxamide, N-(1-azabicyclo[2.2.2]oct-3-yl)-7-propylpyrazolo[1,5-a]pyridine-3-carboxamide, 1-azabicyclo[2.2.2]oct-3-yl 7-methylpyrazolo[1,5-a]-pyridine-3-carboxylate, 1-azabicyclo[2.2.2]oct-3-yl 2,7-dimethylpyrazolo[1,5-a]pyridine-3-carboxylate, 1-azabicyclo[2.2.2]oct-3-yl 7-ethylpyrazolo[1,5-a]-pyridine-3-carboxylate, and 1-azabicyclo[2.2.2]oct-3-yl 7-propylpyrazolo[1,5-a]pyridine-3-carboxylate, or a salt thereof.

4. The derivative or salt of claim 1, which is a compound selected from the group consisting of endo-8-methyl-8-azabicyclo[3.2.1]oct-3-yl pyrazolo[1,5-a]-pyridine-3-carboxylate, endo-8-methyl-8-azabicyclo[3.2.-1]oct-3-yl 7-methylpyrazolo[1,5-a]pyridine-3-carboxylate, endo-8-methyl-8-azabicyclo[3.2.1]oct-3-yl 2-methylpyrazolo[1,5-a]pyridine-3-carboxylate, endo-8-methyl-8-azabicyclo[3.2.1]oct-3-yl 4-methylpyrazolo[1,5-a]pyridine-3-carboxylate, endo-8-methyl-8-azabicyclo[3.2.1]oct-3-yl 5-methylpyrazolo[1,5-a]pyridine3-carboxylate, endo-N-(8-methyl-8-azabicyclo[3.2.1]oct3-yl-7-methylpyrazolo[1,5-a]pyridine-3-carboxamide, and endo-N-(9-methyl-9-azabicyclo[3.3.1]non-3-yl)-7-methylpyrazolo[1,5-a]pyridine-3-carboxamide, or a salt thereof.

5. A pyrazolo[1,5-a]pyridine-3-carboxylic acid derivative represented by the following formula (I):

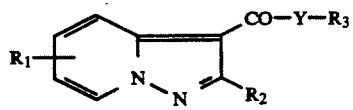

wherein $R_1$ and $R_2$ individually mean a hydrogen atom or a lower alkyl group, $R_3$ denotes a group represented by the following formula:

and Y stands for —O— or —NH—, or a salt thereof.

6. A pyrazolo[1,5-a]pyridine-3-carboxylic acid derivative represented by the following formula (I):

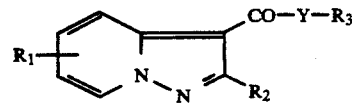

wherein $R_1$ and $R_2$ individually mean a hydrogen atom or a lower alkyl group, $R_3$ denotes a group represented by the following formula:

wherein Z means a lower alkyl group and n stands for an integer of 2 or 3, and Y stands for —O— or —NH—, or a salt thereof.

7. The antagonist of claim 1, wherein the pyrazolo[1,5-a]pyridine-3-carboxylic acid derivative is a compound selected from the group consisting of optically active or racemic N-(1-azabicyclo[2.2.2]oct-3-yl)-pyrazolo[1,5-a]pyridine-3-carboxamide, N-(1-azabicyclo[2.2.2]oct-3-yl)-5-methylpyrazolo[1,5-a]-pyridine-3-carboxamide, N-(1-azabicyclo[2.2.2]oct-3-yl)-7-methylpyrazolo[1,5-a]pyridine-3-carboxamide, N-(1-azabicyclo[2.2.2]oct-3-yl)-2-methylpyrazolo[1,5-a]-pyridine-3-carboxamide, N-(1-azabicyclo[2.2.2]oct-3-yl)-2,7-dimethylpyrazolo[1,5-a]pyridine-3-carboxamide, N-(1-azabicyclo[2.2.2]oct-3-yl)-7-ethylpyrazolo[1,5-a]-pyridine-3-carboxamide, N-(1-azabicyclo[2.2.2]oct-3-yl)-7-pr-opylpyrazolo[1,5-a]pyridine-3-carboxamide, 1-azabicyclo[2.2.2]oct-3-yl 7-methylpyrazolo[1,5-a]-pyridine-3-carboxylate, 1-azabicyclo[2.2.2]oct-3-yl 2,7-dimethylpyrazolo[1,5-a]pyridine-3-carboxylate, 1-azabicyclo[ 2.2.2]oct-3-yl 7-ethylpyrazolo[1,5-a]-pyridine-3-carboxylate, and 1-azabicyclo[2.2.2]oct-3-yl 7-propylpyrazolo[1,5-a]pyridine-3-carboxylate, or a salt thereof.

8. The antagonist of claim 2, wherein the pyrazolo[1,5-a]pyridine-3-carboxylic acid derivative is a compound selected from the group consisting of endo-8-methyl-8-azabicyclo[3.2.1]oct-3-yl pyrazolo[1,5-a]-pyridine-3-carboxylate, endo-8-methyl-8-azabicyclo[3.2.-1]oct-3-yl 7-methylpyrazolo[1,5-a]pyridine-3-carboxylate, endo-8-methyl-8-azabicyclo[3.2.1]oct-3-yl 2-methylpyrazolo[1,5-a]pyridine-3-carboxylate, endo-8-methyl-8-azabicyclo[3.2.1]oct-3-yl 4-methylpyrazolo[1,5-a]pyridine-3-carboxylate, endo-8-methyl-8-azabicyclo[3.2.1]oct-3-yl 5-methylpyrazolo[1,5-a]pyridine3-carboxylate, endo-N-(8-methyl-8-azabicyclo[3.2.1]oct3-yl-7-methylpyrazolo[1,5-a]pyridine-3-carboxamide, and endo-N-(9-methyl-9-azabicyclo[3.3.1]non-3-yl)-7-methylpyrazolo[1,5-a]pyridine-3-carboxamide, or a salt thereof.

* * * * *